(12) United States Patent
Voda

(10) Patent No.: US 6,595,983 B2
(45) Date of Patent: Jul. 22, 2003

(54) GUIDE OR DIAGNOSTIC CATHETER FOR RIGHT CORONARY ARTERY

(76) Inventor: Jan K. Voda, 1404 Camden Way, Oklahoma City, OK (US) 73116

(*) Notice: Subject to any disclaimer, the term of this patent is extended or adjusted under 35 U.S.C. 154(b) by 210 days.

(21) Appl. No.: 09/732,059

(22) Filed: Dec. 7, 2000

(65) Prior Publication Data

US 2002/0103474 A1 Aug. 1, 2002

(51) Int. Cl.$^7$ ............................................. A61M 25/00
(52) U.S. Cl. ....................................... 604/530; 604/523
(58) Field of Search ................. 604/508, 522, 604/523, 285, 500, 48, 530

(56) References Cited

U.S. PATENT DOCUMENTS

| | | | |
|---|---|---|---|
| 3,935,857 A | 2/1976 | Co | 128/2.05 |
| 3,938,501 A | 2/1976 | Erikson | 128/2 A |
| 4,020,829 A | 5/1977 | Willson et al. | 128/2 M |
| 4,033,331 A | 7/1977 | Guss et al. | 128/2 M |
| 4,117,836 A | 10/1978 | Erikson | 128/2.05 R |
| 4,169,464 A | 10/1979 | Obrez | 128/657 |
| 4,195,637 A | 4/1980 | Grüntzig et al. | 128/348 |
| 4,292,976 A | 10/1981 | Banka | 128/656 |
| 4,430,083 A | 2/1984 | Ganz et al. | 604/283 |
| 4,547,193 A | 10/1985 | Rydell | 604/282 |
| 4,551,292 A | 11/1985 | Fletcher et al. | 264/139 |
| 4,563,181 A | 1/1986 | Wijayarathna et al. | 604/280 |
| 4,568,338 A | 2/1986 | Todd | 604/281 |
| 4,581,017 A | 4/1986 | Sahota | 604/101 |
| 4,582,181 A | 4/1986 | Samson | 128/348.1 |
| 4,616,653 A | 10/1986 | Samson et al. | 128/344 |
| 4,733,669 A | 3/1988 | Segal | 128/663 |
| 4,738,667 A | 4/1988 | Galloway | 604/281 |
| 4,747,840 A | 5/1988 | Ladika et al. | 604/281 |
| 4,748,982 A | 6/1988 | Horzewski et al. | 128/344 |
| 4,762,129 A | 8/1988 | Bonzel | 128/344 |
| 4,771,777 A | 9/1988 | Horzewski et al. | 128/344 |

(List continued on next page.)

FOREIGN PATENT DOCUMENTS

| | | |
|---|---|---|
| EP | 0 132 344 A2 | 1/1985 |
| EP | 0 256 478 A1 | 2/1988 |
| EP | 0 277 366 A1 | 8/1988 |
| EP | 0 323 738 A2 | 7/1989 |
| WO | WO 92/12754 | 8/1992 |

OTHER PUBLICATIONS

*PTCA in Perspective*, USCI/Technical Perspective [Block, P.C. et al., USCI Division, C. R. Bard, Inc., Billerica, Mass., pp. 23–42 (1986)].

King, S. B., III, Douglas, J. S., Jr. and Gruentzig, A. R.: *Coronary Arteriography and Angioplasty*, McGraw–Hill, New York, Chapter 17, "Percutaneous Transluminal Coronary Angioplasty," pp. 433–451 (1985).

Amplatz, K., Formanek, G., Stanger, P. and Wilson, W.: "Mechanics of Selective Coronary Artery Catheterization via Femoral Approach," *Radiology 89: 1040–1047*, Dec., 1967.

USCI "USCI® Grüntzig Dilaca™ Coronary Dilatation Equipment" Brochure, C. R. Bard, Inc. (1990) (4 pages).

(List continued on next page.)

*Primary Examiner*—Henry Bennett
(74) *Attorney, Agent, or Firm*—McAfee & Taft

(57) ABSTRACT

A torqueable, three-dimensionally preformed guide or diagnostic catheter to selectively engage the ostium of a right coronary artery in a human includes: a torque-transmitting proximal shaft that receives manipulation by a user outside a human body in which the catheter is used; and a distal shaft that is responsive to torque transmitted by the proximal shaft. The distal shaft includes a preformed support section having at least a segment that abuts a posterior interior surface of the ascending aorta of the human body. The distal shaft also includes a preformed ostium entry section extending from the support section. In one implementation, the ostium entry section transitions from the support segment abutting the aortic wall to a distal tip end by way of at least two angles which provide smoother transition than a single sharp angle.

6 Claims, 2 Drawing Sheets

U.S. PATENT DOCUMENTS

| | | | |
|---|---|---|---|
| 4,781,682 A | 11/1988 | Patel | 604/96 |
| 4,784,639 A | 11/1988 | Patel | 604/53 |
| 4,790,831 A | 12/1988 | Skribiski | 604/282 |
| 4,813,930 A | 3/1989 | Elliott | 604/53 |
| 4,820,349 A | 4/1989 | Saab | 128/344 |
| 4,822,345 A | 4/1989 | Danforth | 604/282 |
| 4,867,174 A | 9/1989 | Skribiski | 128/772 |
| 4,877,031 A | 10/1989 | Conway et al. | 128/344 |
| 4,882,777 A | 11/1989 | Narula | 604/281 |
| 4,883,058 A | 11/1989 | Ruiz | 128/654 |
| 4,886,506 A | 12/1989 | Lovgren et al. | 604/280 |
| 4,896,670 A | 1/1990 | Crittenden | 606/194 |
| 4,898,577 A | 2/1990 | Badger et al. | 604/53 |
| 4,898,591 A | 2/1990 | Jang et al. | 604/282 |
| 4,909,787 A | 3/1990 | Danforth | 604/95 |
| 4,917,103 A | 4/1990 | Gambale et al. | 128/772 |
| 4,922,923 A | 5/1990 | Gambale et al. | 128/772 |
| 4,925,445 A | 5/1990 | Sakamoto et al. | 604/95 |
| 4,935,004 A | 6/1990 | Cruz | 604/29 |
| 4,935,017 A | 6/1990 | Sylvanowicz | 604/280 |
| 4,950,228 A | 8/1990 | Knapp, Jr. et al. | 604/8 |
| 4,973,306 A | 11/1990 | Ruiz | 604/53 |
| 4,976,691 A | 12/1990 | Sahota | 604/96 |
| 4,981,477 A | 1/1991 | Schon et al. | 604/264 |
| 4,983,166 A | 1/1991 | Yamawaki | 604/96 |
| 4,994,032 A | 2/1991 | Sugiyama et al. | 604/96 |
| 5,000,743 A | 3/1991 | Patel | 606/194 |
| 5,016,640 A | 5/1991 | Ruiz | 128/658 |
| 4,762,129 A | 7/1991 | Bonzel | 606/194 |
| 5,031,636 A | 7/1991 | Gambale et al. | 128/772 |
| 5,035,686 A | 7/1991 | Crittenden et al. | 604/96 |
| 5,040,548 A | 8/1991 | Yock | 128/898 |
| 5,044,369 A | 9/1991 | Sahota | 128/658 |
| 5,045,072 A | 9/1991 | Castillo et al. | 604/280 |
| 5,058,595 A | 10/1991 | Kern | 128/662.06 |
| 5,059,197 A | 10/1991 | Urie et al. | 606/116 |
| 5,061,273 A | 10/1991 | Yock | 606/194 |
| 5,098,412 A | 3/1992 | Shiu | 604/280 |
| 5,122,125 A | 6/1992 | Deuss | 604/282 |
| 5,135,535 A | 8/1992 | Kramer | 606/194 |
| 5,154,725 A | 10/1992 | Leopold | 606/194 |
| 5,163,921 A | 11/1992 | Feiring | 604/247 |
| 5,195,971 A | 3/1993 | Sirhan | 604/96 |
| 5,195,990 A | 3/1993 | Weldon | 604/281 |
| 5,203,776 A | 4/1993 | Durfee | 604/264 |
| 5,215,540 A | 6/1993 | Anderhub | 604/281 |
| 5,232,445 A | 8/1993 | Bonzel | 604/96 |
| 5,279,562 A | 1/1994 | Sirhan et al. | 604/96 |
| 5,299,574 A | 4/1994 | Bower | 128/658 |
| 5,306,263 A | * 4/1994 | Voda | 604/281 |
| 5,401,258 A | 3/1995 | Voda | 604/281 |
| 5,445,625 A | 8/1995 | Voda | 604/281 |
| 5,846,229 A | * 12/1998 | Berg | 604/281 |
| 5,868,700 A | * 2/1999 | Voda | 604/49 |
| 5,980,502 A | * 11/1999 | Berg | 604/508 |
| 6,083,213 A | * 7/2000 | Voda | 604/500 |
| 6,110,163 A | * 8/2000 | Voda | 604/523 |
| 6,120,495 A | 9/2000 | Voda | |

OTHER PUBLICATIONS

USCI "Positrol II® and Nycore™ Cardiovascular Catheters" Brochure, pp. 1–21.

Arani, "A New Catheter for Angioplasty of the Right Coronary Artery and Aorto–Coronary Bypass Grafts," *Catheterization and Cardiovascular Diagnosis* 11:647–653 (1985).

voda, Jan K., "Angled Tip of the Steerable Guidewire and Its Usefulness in Percutaneous Transluminal Coronary Angioplasty," *Catheterization and Cardiovascular Diagnosis* 13:204–210 (1987).

Mallinckrodt Medical, Inc., "Diagnostic Catheters" Brochure (1990)(1 page).

USCI "KIFA Products" brochure, pp. 1–12, Jun., 1974.

USCI "KIFA Catheterization Equipment" Brochure, pp. 1–7 (1967).

Medi–Tech® Boston Scientific Corporation "Imager Angiographic Catheters" Brochure, Oct., 1990 (4 pages).

Bourassa, M. G. Lespérance, J. and Campeau, L.: "Selective Coronary Arteriography by the Percutaneous Femoral Artery Approach," Montreal Heart Institute, Montreal, Quebec, Canada, vol. 107, No. 2, pp. 377–383, Oct., 1969.

USCI Video Tape, "Select Curve Guiding Catheter: Cannulating the Right Coronary Artery" (1988).

Wiseguideu ART3.0 guide catheter, SciMed Life Systems, Inc., Maple Grove, Minnesota (2 sheets) (undated but admitted to be prior art).

Williams Right WR Angiographic Catheter, Boston Scientific SciMed, Inc., Maple Grove, Minnesota (undated but admitted to be prior art).

Judkins, M. P., "Percutaneous Transfemoral Selective Coronary Arteriography," *Radiologic Clinics of North America*, vol. VI, No. 3, pp. 467–492, Dec., 1968.

Carr, M. L., "The Use of the Guiding Catheter in Coronary Angioplast: The Technique of Manipulating Catheters to Obtain the Necessary Power to Cross Tight Coronay Stenosis," *Catherization and Cardiovascular Diagnosis* 12:189–197 (1986).

King, S. B. III, and Douglas, J. S., Jr.: *Coronary Arteriography and Angioplasty*, McGraw–Hill, New York, Chapter 7, Judkins, M. P. and Judkins, E., "Coronary Arteriography and Left Ventriculography: Judkins Technique," pp. 182–238 (1985).

* cited by examiner

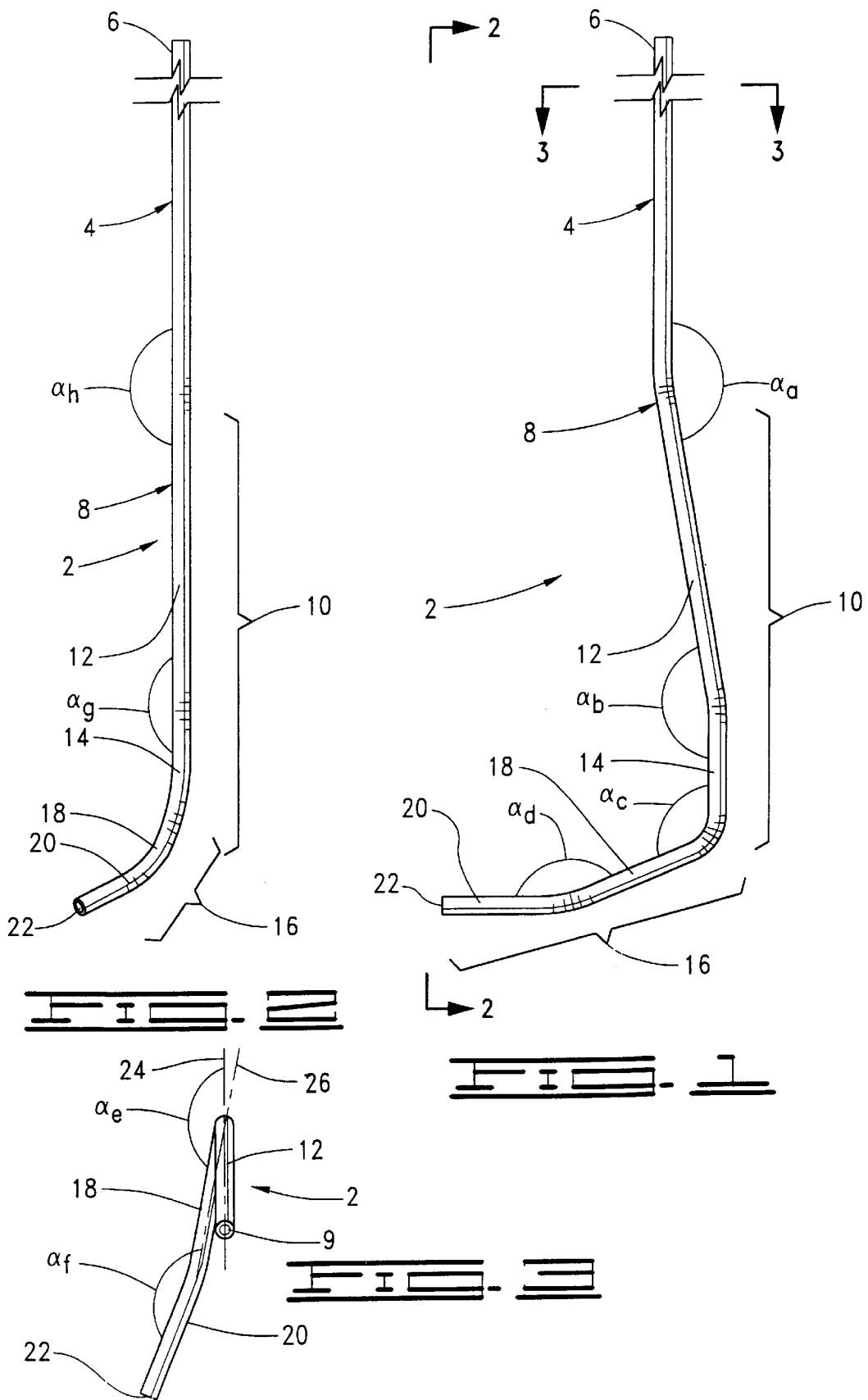

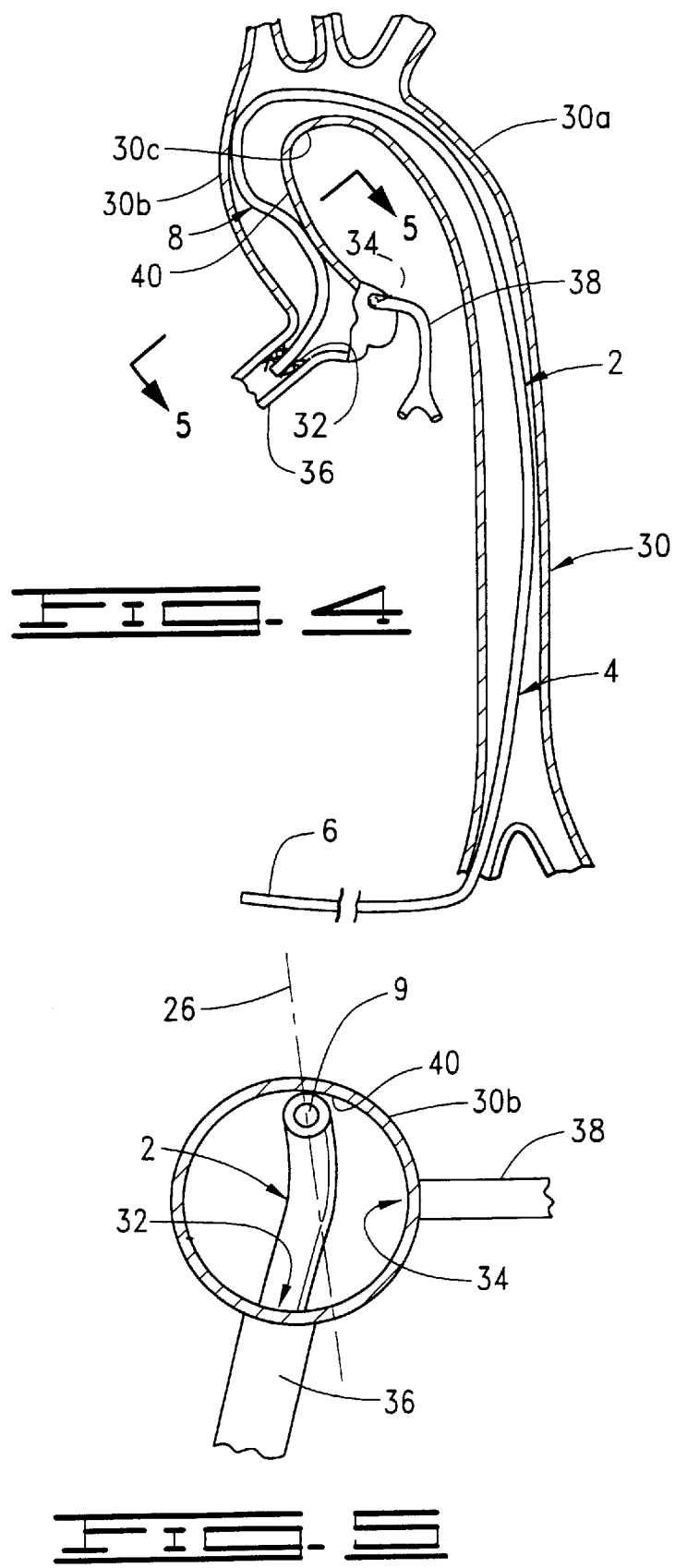

US 6,595,983 B2

GUIDE OR DIAGNOSTIC CATHETER FOR RIGHT CORONARY ARTERY

BACKGROUND OF THE INVENTION

This invention relates generally to catheters for right coronary arteries and more particularly to a preformed, torqueable guide or diagnostic catheter that has a distal segment to abut an inside surface of an ascending aorta and that also has a preformed three dimensional distal portion to facilitate entry of a distal tip into the ostium of a right coronary artery extending from the ascending aorta.

The use of catheters in diagnosing and treating vessels in a human body is well known. One particular known therapeutic use of catheters is in performing percutaneous translumenal coronary angioplasty (PTCA). One technique for performing PTCA in a right coronary artery includes inserting a guide catheter into a femoral artery and advancing the guide catheter such that its distal tip moves through that artery, up the descending aorta, and ultimately into the ostium of the right coronary artery. A balloon catheter is then pushed through the guide catheter into the right coronary artery for use in known manner. As an example of a diagnostic use, a diagnostic catheter can be similarly placed and then used to conduct a radiopaque dye injected in known manner.

There are known types of catheters designed for the right coronary artery. However, there remains the need for a new type of catheter that can be readily used with different right coronary artery morphologies found in human patients. There is the particular need for a preformed, torqueable guide or diagnostic catheter to which torque can be applied from the proximal end and transmitted to the distal end and which has a preformed three-dimensional distal end portion having a tip and shaped such that the tip readily enters the ostium of the right coronary artery upon the initial placement of the catheter or when suitable torque is applied to the proximal end of the catheter.

SUMMARY OF THE INVENTION

The present invention meets the aforementioned needs by providing a novel and improved catheter for a right coronary artery and especially a preformed, torqueable guide or diagnostic catheter to selectively engage the ostium of a right coronary artery in a human. The catheter of the present invention has a distal tip that can be readily placed in the ostia of right coronary arteries across a range of morphologies for such arteries. The structure of the catheter is such that it allows a relatively long, atraumatic tip to be used while diminishing the rotational manipulation that may be needed to engage the tip in the ostium, which provides for easier, less traumatic use of the catheter.

Such a preformed, torqueable guide or diagnostic catheter as defined by the present invention to selectively engage the ostium of a right coronary artery in a human comprises a proximal shaft having a proximal end to receive manipulation by a user outside a human body in which the catheter is used, wherein the proximal shaft transmits torque applied at the proximal end. This catheter further comprises a distal shaft extending from the proximal shaft opposite the proximal end of the proximal shaft such that the distal shaft is responsive to torque transmitted by the proximal shaft. The distal shaft includes a preformed support section having at least a segment thereof which abuts an interior surface of the ascending aorta of the human body when the catheter is in place within the human body. The distal shaft also includes a preformed ostium entry section extending from the support section. In at least an initial position of the catheter outside the human body with the support section of the catheter in a plane parallel to a frontal plane of the body, the ostium entry section of a preferred embodiment lies posteriorly of that plane when the preformed ostium entry section extends rightwardly, relative to the human body, from the preformed support section.

A catheter for a right coronary artery in accordance with the present invention can also be defined as comprising: a proximal shaft having a proximal end to receive manipulation by a user outside a human body in which the catheter is used; and a distal shaft extending from the proximal shaft opposite the proximal end of the proximal shaft. The distal shaft includes a preformed support section to abut a posterior interior surface of the ascending aorta of the human body. This support section includes: a transition segment connected to the proximal shaft at a first bend initially forming an included angle of between 135° and 175°, wherein the transition segment is initially substantially linear; and an abutment segment connected to the transition segment at a second bend initially forming an included angle of between 135° and 175°, wherein the abutment segment is initially substantially linear. The distal shaft also includes a preformed ostium entry section extending from the preformed support section. The preformed ostium entry section includes: a first segment connected to the abutment segment at a third bend initially forming an included angle of between 80° and 160°, wherein the first segment is initially substantially linear; a second segment connected to the first segment at a fourth bend initially forming an included angle of between 100° and 170°, wherein the second segment is initially substantially linear; and wherein the first and second segments are initially offset from an imaginary plane defined by the transition and abutment segments of the preformed support section. In a particular implementation, the first segment is disposed at an initial angle of 130° to 180° relative to one such imaginary plane; and the second segment is disposed at an initial angle of 120° to 180° from a plane defined by the first segment and the abutment segment of the preformed support section. In a more specific implementation, the transition segment has a length between 20 millimeters and 80 millimeters, the abutment segment has a length between 10 millimeters and 40 millimeters, the first segment has a length between 10 millimeters and 40 millimeters, and the second segment has a length between 10 millimeters and 40 millimeters. The second segment terminates at a distal tip which enters the ostium of a right coronary artery when the catheter is properly placed in the human body. There may be another bend between the transition segment and the proximal shaft of between 140° and 180° and another bend between the abutment segment and the transition segment of between 140° and 180°.

Therefore, from the foregoing, it is a general object of the present invention to provide a novel and improved catheter for a right coronary artery and especially a preformed, torqueable guide or diagnostic catheter to selectively engage the ostium of a right coronary artery in a human. Other and further objects, features and advantages of the present invention will be readily apparent to those skilled in the art when the following description of the preferred embodiments is read in conjunction with the accompanying drawings.

BRIEF DESCRIPTION OF THE DRAWINGS

FIG. 1 is a side or lateral view of a preferred embodiment of the present invention.

FIG. 2 is an anterior-posterior view of the preferred embodiment as taken along line 2—2 shown in FIG. 1.

FIG. 3 is a view of the preferred embodiment as taken along line 3—3 shown in FIG. 1.

FIG. 4 schematically illustrates aortic and left and right coronary arterial structures for a human body in which a catheter as shown in FIGS. 1-3 is placed.

FIG. 5 is a view along line 5—5 in FIG. 4.

DETAILED DESCRIPTION OF THE INVENTION

A catheter 2 for a right coronary artery in accordance with the present invention is illustrated in FIGS. 1-3. The catheter 2 comprises a proximal shaft 4 having a proximal end 6 to receive manipulation by a user (not shown) outside a human body in which the catheter 2 is used. The catheter 2 further comprises a distal shaft 8 extending from the proximal shaft 4 opposite the proximal end 6. At least one lumen 9 extends through the shafts 4, 8 to permit passage of other devices (e.g., a balloon catheter when catheter 2 is a guide catheter) or substances (e.g., a radiopaque dye when the catheter is a diagnostic catheter).

The distal shaft 8 includes a preformed support section 10 which both longitudinally and laterally supports a more distal portion of the catheter terminating in a tip 22. A transition segment 12, connected to the proximal shaft 4 at a first bend or curve initially forming an included angle $\alpha_a$ of between 135° and 175° or thereabouts, provides longitudinal and lateral support for the distal tip 22 so as to provide an offset from the axis of the proximal shaft 4 whereby the tip 22 section can be relatively long. Stated another way, the transition segment 12 enables a longer distal tip to function as a shorter tip in passing through the body vessels and into the ostium of the right coronary artery, while maintaining the more gentle curve of a long tip when in the ostium, thereby facilitating the ability to move other equipment or substances through the bend and into the artery. Length in the tip compensates for the offset used to enable lateral support, and length facilitates more gradual angular transitions; however, tip length can make torquing more difficult if it causes the tip to drag against the aortic wall, but in this case the relatively posterior (when positioned as illustrated in FIGS. 4 and 5) offset effectively shortens the "torque length" of the tip section and the tip. The transition segment 12 preferably is initially substantially linear and has a length between 20 millimeters and 80 millimeters (or thereabouts) in the preferred embodiment. "Initially" or "initial" as used here and elsewhere, including the claims, with regard to angularity or linearity pertains to a relaxed state of the catheter or its elements after the catheter has been manufactured but before it has been placed in use in a human body. "About" or "thereabouts" as used here and elsewhere, including the claims, with regard to angularity or linearity encompasses small deviations from the stated range endpoints. Even an absolute range encompasses deviations due to engineering tolerances. Furthermore, references to angles, bends, curves and the like in this description and in the claims are not to be taken as excluding various transitions from one segment to another; that is, these may be linearly sharp or distinct transitions, but may be, and preferably are, radiused or smooth curvilinear transitions.

The preformed support section 10 also comprises an abutment segment 14 connected to the transition segment 12 at a second bend or curve initially forming an included angle $\alpha_b$ of between 135° and 175° or thereabouts. The abutment segment 14 preferably is initially substantially linear and has a length between 10 millimeters and 40 millimeters or thereabouts in the preferred embodiment. The abutment segment 14 provides support relative to the aortic wall. That is, the segment 14 abuts posteriorly on the interior wall of the ascending aorta when positioned as shown in FIGS. 4 and 5, which provides resistance against the distal tip 22 disengaging the ostium of the right coronary artery once the catheter is properly positioned. This support is provided along the length of the segment 14 rather than at only a small point contact, whereby more stable support is provided by the segment 14.

The distal shaft 8 also includes a preformed ostium entry section 16 extending from the preformed support section 10 and terminating at the tip 22. The preformed ostium entry section 16 includes a first segment 18 connected to the abutment segment 14 at a third bend or curve initially forming an included angle $\alpha_c$ of between 80° and 160° or thereabouts. The first segment 18 preferably is initially substantially linear and has a length between 10 millimeters and 40 millimeters or thereabouts in the preferred embodiment.

The preformed ostium entry section 16 further has a second segment 20 connected to the first segment 18 at a fourth bend or curve initially forming an included angle $a_d$ of between 100° and 170° or thereabouts. The second segment terminates at the distal tip 22. The second segment 20 preferably is initially substantially linear and has a length between 10 millimeters and 40 millimeters or thereabouts (with the tip 22 being about 5 millimeters long) in the preferred embodiment.

The first and second segments 18, 20 of this tip section that direct tip 22 into the ostium of the right coronary artery are initially offset from an imaginary plane 24 containing the transition and abutment segments 12, 14 of the preformed support section 10 in the orientation shown in FIG. 3, thereby making the catheter 2 into what is referred to as a three-dimensional catheter (i.e., a shape or configuration outside more than a single principal plane). In at least an initial position of this particular configuration outside the human body, the segments 18, 20 are preformed to lie only posteriorly of the plane 24 when the plane 24 is in front of and parallel to a frontal plane of the human body and when the preformed ostium entry section extends rightwardly (relative to viewing from the human body) from the preformed support section (this would place the human to the left of the catheter 2 in FIG. 2 but facing to the right, i.e., toward the catheter). Once properly placed in the body, the segments 18, 20 extend, from the person's viewpoint, generally forward and to the person's right or clockwise from a plane through the aorta parallel to the sagittal (i.e., midsagittal) plane. Referencing to the catheter 2 itself, in a particular implementation, the first segment 18 is disposed at an initial angle $\alpha_e$ of 130° to 180° or thereabouts relative to the plane 24 of the support section 10, and the second segment 20 is disposed at an initial angle $\alpha_f$ of 120° to 180° or thereabouts from an imaginary plane 26 (FIG. 3) defined by the first segment 18 and the abutment segment 14. The planes 24, 26 are both perpendicular to an imaginary reference plane, such as the plane of the sheet containing FIG. 3.

An advantage of the preformed three-dimensional configuration of the catheter 2 is that it creates a shortened distance through which the distal tip 22 may need to be rotated to engage the ostium of the right coronary artery. This minimizes or reduces the amount of rotation or torque that may need to be applied to the proximal end 6 and transmitted through the length of the shafts 4, 8 to place the tip 22 in the ostium. The preformed three-dimensional configuration also improves the geometry of the catheter entry into the right coronary artery by having a sequence or series of relatively shallower angles rather than a single sharp angle.

Although the foregoing description of the orientation of segments 18, 20 refers to plane 24 as defined by segments 12, 14 as illustrated, it is noted that segments 12 and 14 need not actually lie in this same plane in all embodiments of the present invention. In general, the abutment segment 14 can be at an angle $\alpha_g$ (FIG. 2) of between 140° and 180° or thereabouts relative to the axial line of the transition segment 12 or the plane 24. Similarly, the transition segment 12 can be bent or curved relative to the proximal shaft 4 or the plane 24, such as at an angle $\alpha_h$ (FIG. 2) of between 140° and 180° (or more) or thereabouts. Thus, these segments can be offset at one or two angles or curves (which can also be achieved as rotations) relative to one of the stated references.

The catheter of the present invention can be made of known materials and with known techniques. The material or materials of construction may be the same throughout the catheter, or different materials may be used. A typical material is a known type of plastic used in other catheters, and it can be of a type which itself provides sufficient stiffness to have a desired torque-transmitting capability; however, other constructions can be used, a non-limiting example of which is to incorporate a metallic wire or braid in or with the plastic tubing of the catheter body to provide or enhance the torque-transmitting characteristic of the catheter. Preferably the material of construction prevents or reduces trauma as the catheter is moved through the body (this is especially desirable for the tip 22 which preferably is defined by a thin wall made of a very soft material as known in the art). One or more particular combinations of angles and lengths from the aforementioned ranges are selected for manufacturing specific catheters as are suitable for use in a human.

Part of a typical human cardiovascular system is schematically shown in the side or lateral view of FIG. 4 and the indicated sectional view of FIG. 5. This system includes an aorta 30 comprised of a descending aorta 30a, an ascending aorta 30b, and an aortic arch 30c which extends from the descending aorta 30a to the ascending aorta 30b over a curve of approximately 180°. The ascending aorta 30b branches through a right ostium 32 and a left ostium 34 into a right coronary artery 36 and a left coronary artery 38, respectively.

Also represented in FIGS. 4 and 5 is the catheter 2 placed for effective use in the human body. Emplacement of the catheter 2 as shown in FIGS. 4 and 5 usually occurs through a femoral artery using a technique applied to achieve the illustrated positioning of the catheter 2. This positioning includes having the abutment segment 14 of the preformed support section 10 abut an interior surface of the ascending aorta 30b of the human body substantially opposite the ostium 32, which typically is the posterior interior surface 40. If needed, entry of the distal tip 22 into the ostium 32 is obtained by applying torque to the proximal end 6 and transmitting the torque through the proximal shaft 4 and the distal shaft 8. More specifically, the catheter 2 is advanced in conventional manner until the distal tip 22 is slightly above the ostium 32 of the right coronary artery 36. As the proximal end 6 is torqued clockwise, the shafts 4 and 8 rotate in response, and the distal tip 22 rotates and lowers into engagement with the ostium 32. The amount of rotation should be relatively small because of the three-dimensional configuration of the present invention, and engagement with the ostium 32 is secured by the abutment segment 14 engaging the aortic wall, and ease of equipment or substance transmission through the lumen 9 of the catheter 2 is facilitated by the relatively long distal tip 22 as offset by the transition segment 12. Accordingly, the present invention provides a preformed, torqueable catheter, particularly a preformed, torqueable guide or diagnostic catheter, for a right coronary artery.

Thus, the present invention is well adapted to carry out the objects and attain the ends and advantages mentioned above as well as those inherent therein. While preferred embodiments of the invention have been described for the purpose of this disclosure, changes in the construction and arrangement of parts and the performance of steps can be made by those skilled in the art, which changes are encompassed within the spirit of this invention as defined by the appended claims.

What is claimed is:

1. A catheter for a right coronary artery, comprising:
    a proximal shaft having a proximal end to receive manipulation by a user outside a human body in which the catheter is used; and
    a distal shaft extending from the proximal shaft opposite the proximal end of the proximal shaft, the distal shaft including:
        a preformed support section to abut a posterior interior surface of the ascending aorta of the human body, wherein the support section includes:
            a transition segment connected to the proximal shaft at a first bend initially forming an included angle of between 135° and 175°, wherein the transition segment is initially substantially linear; and
            an abutment segment connected to the transition segment at a second bend initially forming an included angle of between 135° and 175°, wherein the abutment segment is initially substantially linear; and
        a preformed ostium entry section extending from the preformed support section, wherein the preformed ostium entry section includes:
            a first segment connected to the abutment segment at a third bend initially forming an included angle of between 80° and 160°, wherein the first segment is initially substantially linear;
            a second segment connected to the first segment at a fourth bend initially forming an included angle of between 100° and 170°, wherein the second segment is initially substantially linear; and
            wherein the first and second segments are initially offset from an imaginary plane defined by the transition and abutment segments of the preformed support section.

2. A catheter as defined in claim 1, wherein:
    the first segment is disposed at an initial angle of 130° to 180° relative to the imaginary plane; and
    the second segment is disposed at an initial angle of 120° to 180° from a plane defined by the first segment and the abutment segment of the preformed support section.

3. A catheter as defined in claim 2, wherein:
    the transition segment has a length between 20 millimeters and 80 millimeters;
    the abutment segment has a length between 10 millimeters and 40 millimeters;
    the first segment has a length between 10 millimeters and 40 millimeters; and
    the second segment has a length between 10 millimeters and 40 millimeters.

4. A catheter as defined in claim 3, wherein the second segment terminates at a distal tip which enters the ostium of a right coronary artery when the catheter is properly placed in the human body.

5. A preformed, torqueable guide or diagnostic catheter to selectively engage the ostium of a right coronary artery in a human, comprising:

a proximal shaft having a proximal end to receive manipulation by a user outside a human body in which the catheter is used, wherein the proximal shaft transmits torque applied at the proximal end; and a distal shaft extending from the proximal shaft opposite the proximal end of the proximal shaft such that the distal shaft is responsive to torque transmitted by the proximal shaft, the distal shaft including:

a preformed support section having at least a segment thereof which abuts an interior surface of the ascending aorta of the human body when the catheter is in place within the human body, wherein the preformed support section includes:

a transition segment connected to the proximal shaft at a first bend initially forming an included angle of between 135° and 175°, wherein the transition segment is initially substantially linear with a length between 20 millimeters and 80 millimeters; and an abutment segment connected to the transition segment at a second bend initially forming an included angle of between 135° and 175°, wherein the abutment segment is initially substantially linear with a length between 10 millimeters and 40 millimeters; and a preformed ostium entry section extending from the preformed support section, wherein the preformed ostium entry section includes:

a first segment connected to the abutment segment at a third bend initially forming an included angle of between 80° and 160°, wherein the first segment is initially substantially linear with a length between 10 millimeters and 40 millimeters;

a second segment connected to the first segment at a fourth bend initially forming an included angle of between 100° and 170°, wherein the second segment is initially substantially linear with a length between 10 millimeters and 40 millimeters; and wherein the first segment is disposed at an initial angle of 130° to 180° relative to a plane of the abutment segment and the second segment is disposed at an initial angle of 120° to 180° from a plane defined by the first segment and the abutment segment such that in at least an initial position of the catheter outside the human body with the transition segment of the preformed support section in a plane parallel to a frontal plane of the human body, the preformed ostium entry section lies posteriorly of such plane when the preformed ostium entry section extends rightwardly, relative to the human body, from the preformed support section.

6. A catheter as defined in claim 5, wherein there is another bend between the transition segment and the proximal shaft of between 140° and 180°, and wherein there is another bend between the abutment segment and the transition segment of between 140° and 180° in a direction such that in said at least initial position of the catheter outside the human body with the transition segment of the preformed support section in the plane parallel to the frontal plane of the body, the abutment segment and the preformed ostium entry section lie posteriorly of such plane when the preformed ostium entry section extends rightwardly, relative to the human body, from the preformed support section.

* * * * *